United States Patent [19]

Laico et al.

[11] Patent Number: 5,027,799

[45] Date of Patent: Jul. 2, 1991

[54] LIMB SUPPORTING DEVICE FOR ARTHROSCOPIC SURGERY

[75] Inventors: Joseph P. Laico, New City; Joseph L. Molino, Valley Cottage, both of N.Y.

[73] Assignee: Lincoln Mills, Inc., New City, N.Y.

[21] Appl. No.: 598,651

[22] PCT Filed: Apr. 19, 1989

[86] PCT No.: PCT/US89/01660

§ 371 Date: Oct. 18, 1990

§ 102(e) Date: Oct. 18, 1990

Related U.S. Application Data

[63] Continuation-in-part of Ser. No. 7,318,811, Mar. 3, 1989, Pat. No. 4,964,400, which is a continuation-in-part of Ser. No. 7,183,636, Apr. 19, 1988, abandoned.

[51] Int. Cl.[5] .......................... A61H 1/02; A61F 5/10

[52] U.S. Cl. .......................................... 128/75; 128/77

[58] Field of Search ................. 128/75, 77, 878, 84 C, 128/87 R, 80 R, 877, 879, 85, 882, 80 A, 84 R, 84 B, 87 C; 5/445

[56] References Cited

U.S. PATENT DOCUMENTS

| | | | |
|---|---|---|---|
| 198,723 | 12/1877 | Woods | 128/84 R |
| 1,699,026 | 1/1929 | Schumacher | 128/84 C |
| 2,020,262 | 11/1935 | Longfellow | 128/84 B |
| 2,302,868 | 11/1942 | Invidiato | 128/87 R |
| 3,662,750 | 5/1972 | Jorgensen | 128/84 C |
| 3,765,411 | 10/1973 | Ward | 128/84 C |
| 3,800,787 | 4/1974 | Rush | 128/84 R |
| 3,850,165 | 11/1974 | Throner | 128/84 C |
| 4,181,125 | 1/1980 | Carlson | 128/75 |
| 4,254,766 | 3/1981 | Kordis | 128/87 R |
| 4,259,949 | 4/1981 | Axelsson | 128/77 |
| 4,323,060 | 4/1982 | Pecheux | 128/84 R |
| 4,534,555 | 8/1985 | McGowen | 128/75 |
| 4,551,872 | 11/1985 | Reed | 5/445 |
| 4,649,907 | 3/1987 | Whitehead | 128/84 C |
| 4,753,228 | 6/1988 | Selner | 128/80 R |

FOREIGN PATENT DOCUMENTS

| | | | |
|---|---|---|---|
| 0920448 | 4/1947 | France | 128/84 C |

*Primary Examiner*—Robert A. Hafer
*Assistant Examiner*—Michael Brown
*Attorney, Agent, or Firm*—Chilton, Alix & Van Kirk

[57] ABSTRACT

A limb holding device designed to be attached to an operating table to immobilize a patient's arm or leg during arthroscopic surgery or the like. It provides for distraction of the hip joint or other joint being worked on, and also provides for reduction and maintenance of position of fractures of the arm or leg. The device includes a pair of vertical upright supports braced by an adjustable connecting bar, and a fork-like member has a canvas or plastic cradle stretched between its two tines, a plurality of straps to immobilize the patient's limb on the cradle, a padded shoe-like or plate-like device to hold the foot firmly, and a handle means to facilitate manipulation of the limb and to place the proper traction forces thereon. A tensiometer is integrated into the fork-like member to allow direct and accurate indication of the traction force being-placed on the limb. Once the desired position of the limb and joint is achieved, the various adjustable clamps and stop nuts may be secured to lock the device in that position during surgery.

16 Claims, 2 Drawing Sheets

LIMB SUPPORTING DEVICE FOR ARTHROSCOPIC SURGERY

CROSS REFERENCE TO RELATED APPLICATIONS

This application is a continuation-in-part of application Ser. No. 318,811 filed Mar. 3, 1989, now U.S. Pat. No. 4,964,403 which is a continuation-in-part of application Ser. No. 183,636 filed Apr. 19, 1988 now abandoned.

BACKGROUND OF THE INVENTION

1. Field of the Invention

This invention relates to a limb holding device designed to immobilize a hip during arthroscopic surgery, and it is also adaptable to most types of leg surgery, as well as for surgery on the arm or shoulder. To function properly in the surgical environment, a limb supporting device must provide firm immobilization of the upper or lower extremity involved in the surgery, allow for the extremity to be moved in any direction and then be firmly fixed in place, and allow the joint involved to be distracted to allow insertion of surgical instruments or the like.

2. Description of the Prior Art

Prior art devices have been cumbersome to use and ineffective in providing a universal range of movement of the limb being treated such that the surgeon may most efficiently and effectively treat the patient.

Examples of such prior art devices include U.S. Pat. No. 3,087,489 issued to H. Gilbert et al on Apr. 30, 1963, entitled "Universal Orthopedic Traction and Holding Device" and U.S. Pat. No. 3,840,166 issued to Tammy et al on Nov. 26, 1974, entitled "Fracture Reduction Device". Both of these patents show cumbersome devices which impede a surgeon's treatment of a limb by causing him to work around the hardware of the apparatus, wherein a portion of the limb being treated may be inaccessible without shifting the position of either the patient or the apparatus, or causing the surgeon to lean completely across the patient's body to treat the limb. Such inconveniencing of and acrobatics by the surgeon are precluded by the limb supporting device of the subject invention.

BRIEF SUMMARY OF THE INVENTION

The invention consists of two L-shaped or straight poles designed to be secured to one end of a standard operating table, with the horizontal or vertical portions of the poles attached to the table sides, and the upright portions extending vertically upward above the table top. The upright portions for the poles are interconnected by an adjustable connecting bar, to which is secured by a universally adjustable clamp a fork-like limb holding member. The two tines of the fork-like member are formed of two telescoping elements, the outer, female portions of the fork being interconnected by an outer base member which includes a post for a foot holder, and the inner, male portions of the fork being interconnected by an inner base member. The open ends of the tines of the fork are interconnected by a canvas or plastic material to comfortably cradle the patient's arm or leg, and attached along the length of the cradle material are a plurality of strap means for immobility and securing the limb. The handle end of the fork is a threaded shaft terminating in a T-handle. Located along the threaded portion of the handle are a threaded handle and associate stop nuts to allow positional and tensional adjustments of the fork member and its cradled limb. A tension measuring device is placed between the inner and outer base members of the fork to indicate directly the tension being applied to the patient's limb. To provide further adaptability of the device, a foot attachment device may be attached to the foot holder post attached to the outer base of the limb holding fork. The foot plate or shoe includes a plurality of straps and cuffs to allow firm attachment of the foot to the post to facilitate rotation, flexion, extension abduction or adduction of the lower extremity.

DETAILED DESCRIPTION OF THE PREFERRED EMBODIMENT

Figure 1:
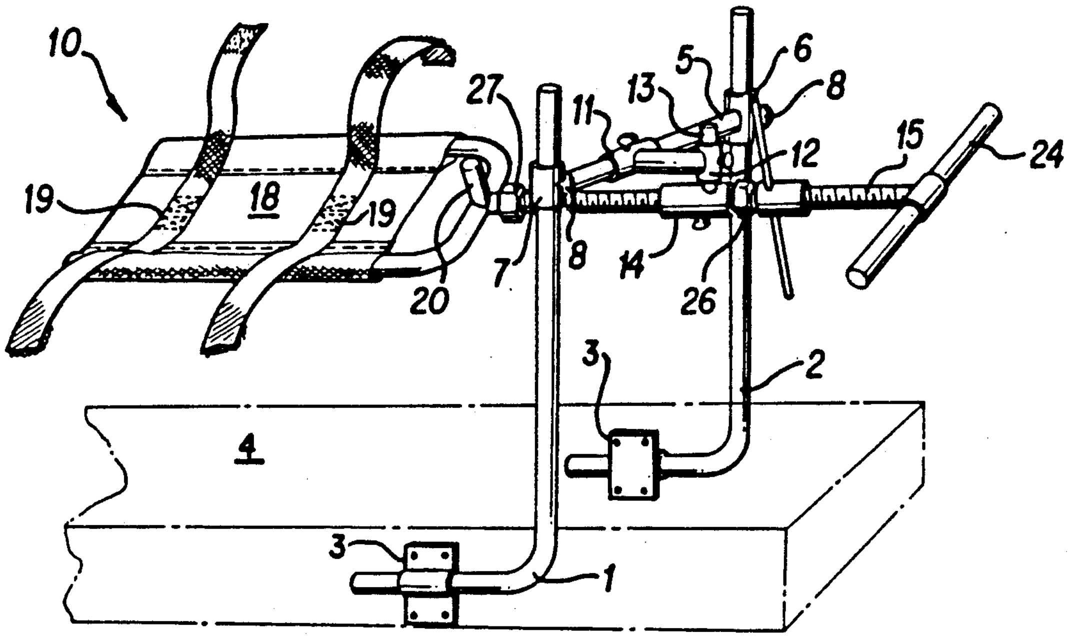
FIG. 1 is a perspective view of the limb supporting device of the invention shown secured to a standard operating table (illustrated in phantom)

Referring now to FIG. 1, the limb supporting device of the subject invention is shown attached to the end of a standard operating table, and positioned for use. The two main L-shaped or straight support bars 1 and 2 are shown with their horizontal or vertical portions secured by clamps 3 to opposite sides of one end of the table 4. The upright portions of bars 1 and 2 extend vertically upward above the surface of table 4. These upright portions are interconnected by connecting bar 5, which includes at either end, an adjustable clamping means 5, 7. As round-section tubing or solid rods are utilized throughout in the construction of this invention, this clamp may take the form of a cylindrical sleeve welded or otherwise attached to the end of connecting bar 5, slid over the top end of the upright portions of bars 1 and 2, and secured by means of a thumbscrew or handle 8 threaded through the sleeve and frictionally engaging the upright bar.

Centrally attached on connecting bar 5 is a two-part clamping apparatus which allows universal movement of limb-supporting fork member 10 attached thereto. This clamping apparatus includes a first sleeve-and-thumbscrew clamp 11 which is secured to connecting bar 5, and second sleeve-and-thumbscrew clamp 12 which is secured to short post 13, and a third sleeve-and-thumbscrew clamp 14 which is secured to the threaded shaft 15 of the fork handle. This elaborate clamping arrangement allows ease of removal and replacement of the entire limb-supporting fork member 10 without disassembly of the entire apparatus. Simply loosening clamp 12 allows removal of post 13, clamp 14 and the entire fork member 10.

Figure 3:
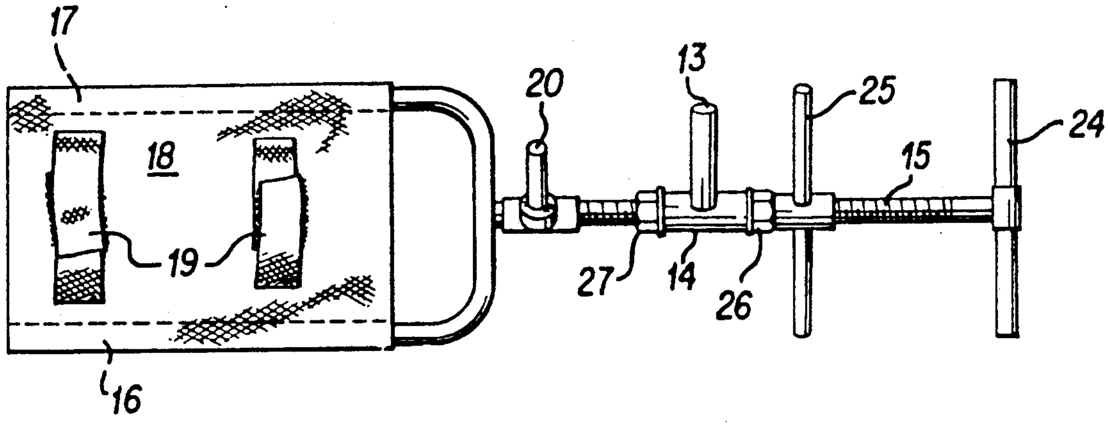
FIG. 3 is a top plan view of the limb supporting fork member removed from its vertical and horizontal support structure for clarity, and including the tension measuring device.

Referring now to FIG. 3, fork member 10 is comprised of female tines 16 and 17 which are interconnected by outer base member 28 and male tines 29 and 30 which are interconnected by inner base member 31. Mounted between inner and outer base members 31 and 28 is a tension measuring device 32. Tensionmeter 32 may be a mechanical or electronic unit, one of many devices available in the marketplace, so long as it is capable of providing an accurate readout of the tension being placed upon the patient's limb supporting device.

Sewn or otherwise attached around and between the female tines 16 and 17 of fork member 10 is a canvas or plastic material 18 which serves to cradle and support the limb of the patient which is to be immobilized. To secure the limb to the cradle, a plurality of straps or cuffs 19 are sewn or otherwise attached along the length of cradle material 18.

Figure 2:
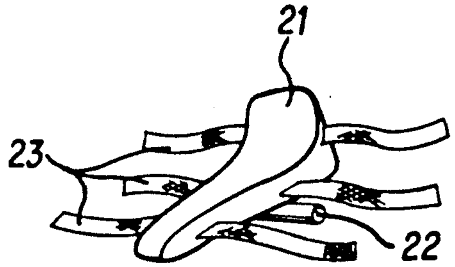
FIG. 2 is a perspective view of the foot plate which may be added to the limb supporting device to aid positioning of a leg.

To further facilitate positioning and securement of a leg to the device, a post 20 is shown welded or otherwise attached centrally to outer base member 28 between fork tines 16 and 17, and extending perpendicular to the plane defined by the tines 16 and 17. To this post 20 may be attached foot plate 21 (FIG. 2) by means of sleeve 22. Foot plate 21 includes a plurality of straps 23 which serve to secure a patient's foot to the plate, thus providing more positive positioning and/or movement of a patient's leg when immobilized using the present invention.

The handle portion of fork member 10 (FIGS. 1 and 3) includes an elongate threaded shaft 15 welded or otherwise secured centrally to inner base member 31 between fork tines 29 and 30, and extending opposite to the direction of the tines parallel thereto, and in the same plane. Shaft 15 terminates in a short, T-shaped handle 24 which is rigidly secured to fork member 10 for ease of rotational manipulation of fork 10 and cradle 18 while supporting a limb. Carried upon threaded shaft 15 are a tension adjusting handle 25 and an associated pair of stop nuts 26 and 27, one nut mounted on either side of sleeve clamp 14. These elements allow for fine adjustment of the traction force exerted on the patient's limb, moving fork member 10 one thread-width at a time for every full revolution of windlass handle 25. Since the outer or female fork tines 16 and 17 are freely slidable over the inner or male tines 29 and 30, the force placed upon the patient's limb will be directly readable on tensionmeter 32.

In use, the entire limb supporting device is attached to an operating table 4 as shown in FIG. 1. The patient is positioned on the table 4 in such a manner that the desired limb rests on cradle material 18. The vertical height, angle of inclination and longitudinal positions of the cradle may be adjusted through sleeve clamps 6, 7, 11, 12, and 14. Once the desired position is achieved, the patient's limb is immobilized by securement of straps 19 about the limb. Additionally, in the case of leg or hip surgery, foot plate 21 (FIG. 2) may be attached to fork member 10 by locating sleeve 22 on post 20, and securing the patient's foot to foot plate 21 by means of straps 23.

Once the limb has been immobilized, coarse adjustments in the traction forces placed on the limb may be made by pushing, pulling or rotating T-handle 24. Final, fine adjustments in the traction forces are achieved through the use of windlass handle 25 and associated stop nuts 26 and 27, with the stop nuts used to rigidly secure the entire device in the position required for surgery. Tensionmeter 32 provides a direct and accurate readout of the traction force being applied to the limb to aid in accurate adjustment by the surgeon. It is obvious from the foregoing description of the use of this device that any minute positional corrections which might be necessary during the course of surgery may be easily achieved by loosening the appropriate clamp or stop nut, making the correction, and securing the device in its new position.

Figure 4:
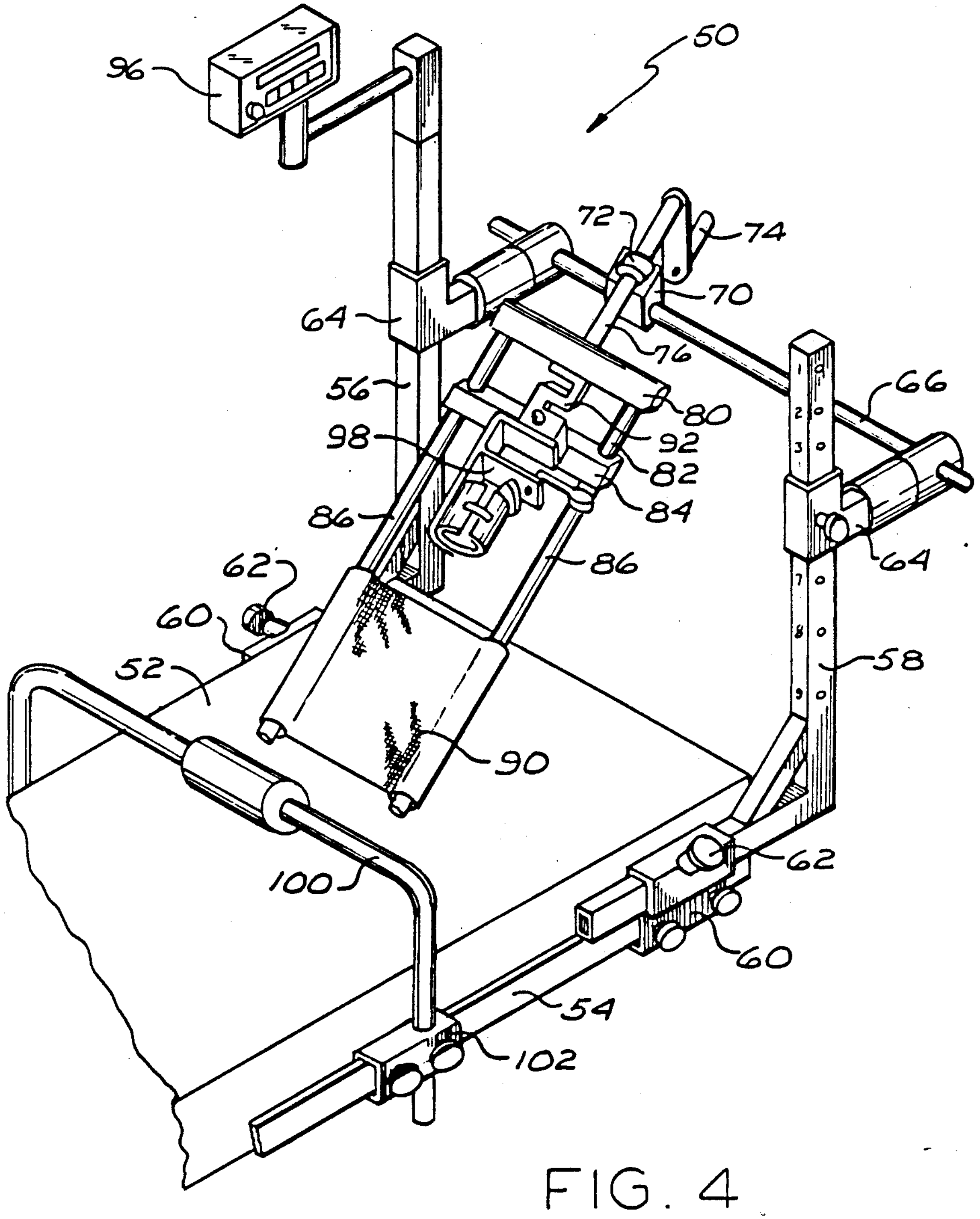
FIG. 4 is a perspective view of a second embodiment of the limb supporting device of the invention shown mounted to a standard operating table.

Referring now to FIG. 4, a second embodiment of a limb supporting device, in accordance with the present invention, is generally designated by the numeral 50. An upright support frame structure for the device comprises generally L-shaped support members 56 and 58. The support members 56 and 58 are secured to rails 54 of a standard operating table 52 by means of table clamps 60. Legs of the support members are received in longitudinal slots of the table clamps and secured by means of clamp screws 62. The selected longitudinal position of the table clamp and the support frame assembly along rails 54 is obtained and the table clamps locked at the selected position.

The support members support bracket connectors 64 connecting with bosses which receive a laterally extending crossbar 66. It should be appreciated that the frame assembly projects in upright relationship above the operating table. A connector block 70 with a knob and shaft through the block to lock the block against crossbar 66 to adjust and isolate lateral and rotational movement is slidably mounted on the crossbar 66. A crank housing 72 is mounted to the top of the connector block. A manually rotatable crank 74 is angularly positionable for varying the transverse displacement or position of a positioning shaft 76.

The positioning shaft 76 connects with a fork member 80 having tines 82. A shaft and knob assembly goes through housing 72 to compress a collar bushing against the inner sleeve to isolate rotational motion of the shaft 76 connecting fork member 80. The tines 82 are telescopically received in tubular tines 86 of an elongated fork-like member 84. A flexible web 90 forms a pair of opposing sleeves which mount over the ends of the tines 86 to provide an adjustable limb receiving web for proximally and distally adjusting the attachment location of the limb. The limb may be secured to the receiving web 90 by fabric adhesive-type straps (not illustrated) attachable below the web 90. An inflatable ankle cuff 98 may also be secured to the base of the fork member 84.

A tensionmeter 92, which may be a load cell, strain gauge or other type of tension measuring device, is disposed between the base members of the fork-like member 80 and the fork-like member 84 for measuring the tension between the telescopic members. It will be appreciated that the tension may be suitably varied by manual actuation of the crank 74 to vary the spatial relationship between the fork-like member 80 and the support frame assembly, including crossbar 66. A display gauge 96 may be mounted to the upper portion of support member 56 and connected via electrical leads with the tensionmeter 92 for indicating the traction tension applied between the fork-like members 80 and 84 (and hence against the supported limb upon suitable attachment). The tensionmeter 92 or strain gauge may be positioned anywhere between the foot and the hip where there are two opposing forces.

It will be appreciated that the limb attachment portion of the device may be essentially universally positionable relative to the crossbar and the operating table for obtaining the proper angular orientation for the limb. A perineal post 100 may also be mounted to opposing rails 54 by means of table clamps 102. The perineal post 100 cooperates with limb supporting device 50 to aid in positioning the patient for hip surgery and in providing an additional vector of force on the perineum and inner portion of the thigh to further aid in separating the hip joint. The perineal post 10 may be adjusted intraoperatively.

This detailed description of the preferred embodiment of the present invention and the specific apparatus described herein may of course be modified or changed in the design, construction or materials thereof without departing from the spirit and scope of this invention, which is limited only by the appended claims.

What is claimed:

1. A limb supporting apparatus for use during surgical procedures or the like comprising:

support means comprising two support members;

mounting means for mounting said support members to an operating table for generally vertical orientation;

crossbar means supported by said support members and extending laterally relative to said support members;

limb supporting means connected to said crossbar means, said limb supporting means comprising first section means for attachment to a limb and second section means displaceable relative to said first section;

tension measurement means disposed between said first and second section means for measuring the amount of tension exerted between said first and second section means; and tension adjustment means for adjusting the tension exerted between said first and second section means comprising a crank and a positioner shaft connecting said second section means, the position of said shaft being responsive to rotatable displacement of said crank.

2. The limb supporting apparatus of claim 1 wherein said limb supporting means comprises a fork-like structure connected to said crossbar means.

3. The limb supporting apparatus of claim 2 wherein said fork-like structure comprises pairs of inner and outer telescoping tines, each pair of said tines inter-connected by respective inner and outer base members, said tension measurement means being disposed between said inner and outer base members.

4. The limb supporting apparatus of claim 1 wherein said tension measurement means includes an analog gauge readout.

5. The limb supporting apparatus of claim 1 wherein said tension measurement means includes a digital readout.

6. The limb supporting apparatus of claim 1 further comprising tension display means mounted to a support member and electrically communicating with said tension measurement means for displaying the tension measurement.

7. A limb supporting apparatus adapted for installation on an operating table for use during surgical procedures or the like comprising:

frame means comprising a frame mountable to an operating table for generally upright disposition above said table;

limb supporting means connecting said frame means for generally universal positioning thereabout, said limb supporting means comprising first section means for attachment to a limb and second section means displaceable relative to said first section means; and tension measurement means comprising a digital readout disposed between said first and second section means for measuring the amount of tension exerted between said first and second section means.

8. The limb supporting apparatus of claim 7 further comprising tension adjustment means for fixably adjusting the tension exerted between said first and second section means.

9. The limb supporting apparatus of claim 7 wherein said limb supporting means comprises a fork-like structure connected to said frame means.

10. The limb supporting apparatus of claim 9 wherein said fork-like structure comprises pairs of inner and outer telescoping tines, each pair of said tines inter-connected by respective inner and outer base members, said tension measurement means being disposed between said inner and outer base members.

11. The limb supporting apparatus of claim 7 wherein said tension measurement means includes an analog gauge readout.

12. The limb supporting apparatus of claim 7 further comprising tension display means mounted to a tension measurement means for displaying the tension measurement.

13. A limb supporting apparatus adapted for installation on an operating table for use during surgical procedures or the like comprising:

frame means comprising a frame mountable to an operating table for generally upright disposition above said table;

limb supporting means connecting said frame means for generally universal positioning thereabout, said limb supporting means comprising first section means for attachment to a limb and second section means displaceable relative to said first section means; and tension adjustment means for adjusting the tension exerted between said first and second section means, said tension adjustment means comprising a rotatable member and a shaft which is variably positioned relative to said frame means in response to said rotatable member.

14. The limb supporting apparatus of claim 13 further comprising clamping means for clamping said limb supporting means in a fixed relationship to said frame means.

15. The limb supporting apparatus of claim 13 wherein said limb supporting means comprises a fork-like structure and a web-like cradle for receiving said limb.

16. The limb supporting apparatus of claim 13 wherein said fork-like structure comprises pairs of inner and outer telescoping tines, each pair of said tines interconnected by respective inner and outer base members, said tension measurement means being disposed between said inner and outer base members.

* * * * *